United States Patent

Grau et al.

[11] Patent Number: 4,788,410
[45] Date of Patent: Nov. 29, 1988

[54] PROCESS FOR CONTROLLING AND/OR GUIDING THE WELD SEAM DURING ARC WELDING AND A PAINT THEREFOR

[75] Inventors: Michael Grau; Bernd Schubert, both of Hamburg, Fed. Rep. of Germany

[73] Assignee: Mankiewicz Gebr. & Co. (GmbH & Co.), Hamburg, Fed. Rep. of Germany

[21] Appl. No.: 71,342

[22] PCT Filed: Sep. 16, 1986

[86] PCT No.: PCT/EP86/00532
§ 371 Date: May 14, 1987
§ 102(e) Date: May 14, 1987

[87] PCT Pub. No.: WO87/01805
PCT Pub. Date: Mar. 26, 1987

[30] Foreign Application Priority Data

Sep. 17, 1985 [DE] Fed. Rep. of Germany ....... 3533145

[51] Int. Cl.⁴ .............................................. B23K 9/12
[52] U.S. Cl. ........................ 219/124.34; 219/130.01
[58] Field of Search ................... 219/130.01, 130.21, 219/124.34; 427/418

[56] References Cited

U.S. PATENT DOCUMENTS 2,823,139 2/1958 Schulze et al. ................... 427/418

FOREIGN PATENT DOCUMENTS 1040821 9/1958 Fed. Rep. of Germany .
278923 11/1970 U.S.S.R. ..................... 219/124.34
421450 8/1974 U.S.S.R. ..................... 219/124.34
901203 7/1962 United Kingdom ........... 219/124.34
1281307 12/1972 United Kingdom .

OTHER PUBLICATIONS

Industrieroboter zum Schweissen und Schneiden from *Bander Bleche Rohro*, 9-1985, 99238-241, (no translation).

Primary Examiner—Clifford C. Shaw
Attorney, Agent, or Firm—Bacon & Thomas

[57] ABSTRACT

A process for the control and/or guidance of welds in electric arc welding wherein a metal or a metal alloy is applied to the edge or surface to be welded of at least one workpiece, with the metal or at least one of the principal alloying metals not being present in the workpiece or at least in slight proportions only, so that a characteristic spectral line emitted by at least one of the metals applied is observed spectroanalytically in the arc and that the weld is controlled and/or the arc guided by means of the spectral data determined.

15 Claims, 1 Drawing Sheet

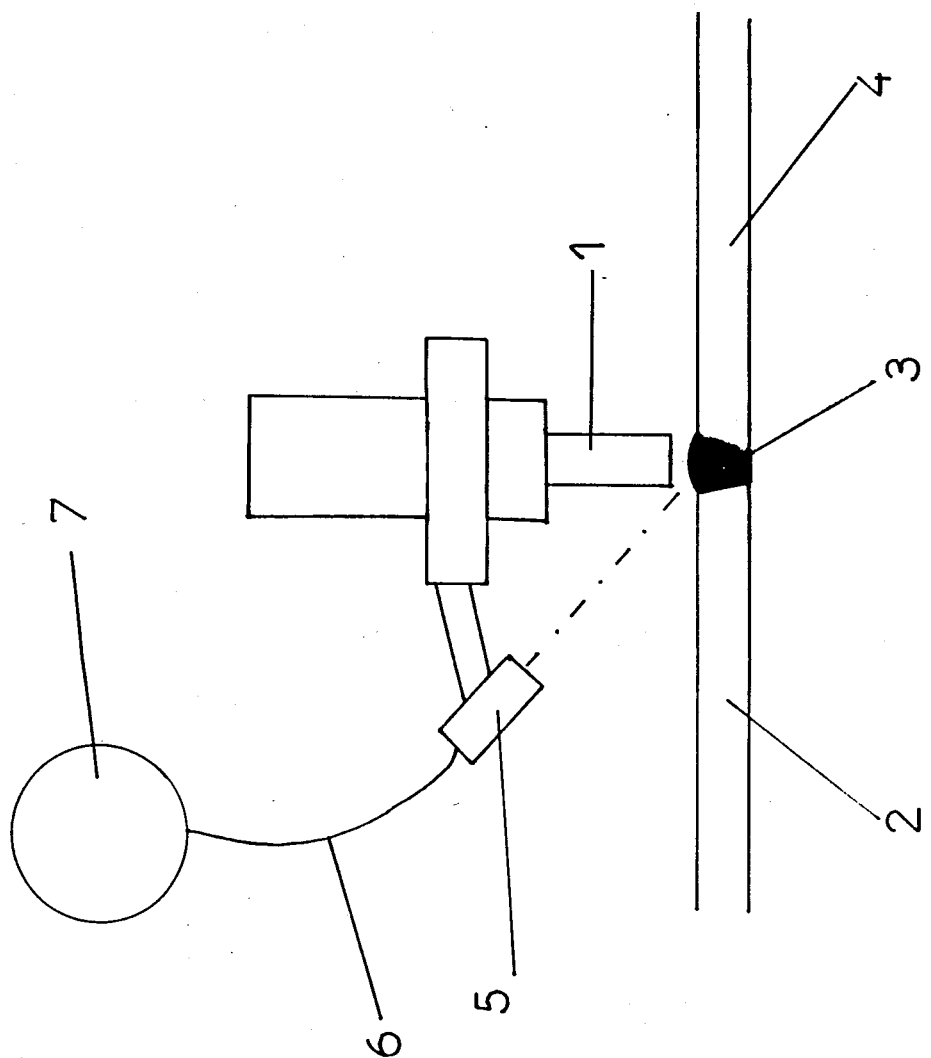

PROCESS FOR CONTROLLING AND/OR GUIDING THE WELD SEAM DURING ARC WELDING AND A PAINT THEREFOR

BACKGROUND OF THE INVENTION

1. Field of the Invention

The invention concerns a process for the control and/or guidance of welds in arc welding and a lacquer to be used in the process.

2. Description of the Prior Art

In order to enhance productivity, save energy and raw materials and to improve the quality of products, attempts are always made to carry out and to control manufacturing processes automatically.

The principal problem of arc welding technology consists of the need to guide the welding arc automatically along the weld joint. This, however, requires the availability of appropriate sensor systems capable of securely following the weld joint in order to automatically assure the positioning of the welding burner in its path following the existing weld joint.

Different sensor systems have already been proposed. A review may be found in the article by P. Drews and G. Starke, "Sensors in Welding technology", Umschau 1985, No. 5, page 296.

In the arc welding of safety parts there exists the further need to control the quality of the weld.

The sensor systems used at the present time for the guidance of the arc and to control quality, are technically involved and thus very expensive. In the case of certain parts, such as for example deep drawing sheets, these known sensor systems cannot be used at all.

SUMMARY OF THE INVENTION

It is the object of the present invention to provide a welding process making possible the simple guidance of the weld or the burner, respectively, and/or the control of the weld during electric arc welding. A coating agent, in particular a lacquer capable of being used in such a process, is to be provided further.

The object of the invention is thus a process characterized in that a metal or a metal alloy is applied to the edge of a surface to be welded of at least one workpiece, with the metal or at least one of the principal alloying metals, not being present in the workpiece or only in small proportions, in that at least one characteristic spectral line in the arc emitted by at least one metal applied to the workpiece is observed spectroanalytically, and that by means of the spectral data obtained the weld is controlled and/or the arc guided.

BRIEF DESCRIPTION OF THE DRAWING

The single FIGURE of the drawing schematically depicts an apparatus for practicing the invention.

DETAILED DESCRIPTION OF THE INVENTION

Due to the high temperature of the arc, not only part of the metals present in the material and the weld wire is evaporating, but also a part of the metals applied. Simultaneously, the evaporated metals are excited by the arc and emit a spectrum characteristic of them. The arc thus serves as a spectroanalytical light source.

The emission spectrum emitted by the individual metals is known. In the process according to the invention the light of the arc is spectroanalytically decomposed. The characteristic spectral line emitted by the metal applied (which for example is present in the elemental form or as an alloy) is measured. Thus for example the intensity of this spectral line is determined.

The apparatus to carry out such an emission spectral analysis and to determine the intensity of the spectral line is known to those skilled in the art and is described for example in "Fundamentals and methods of chemical emission spectral analysis" by R. Mannkopff and G. Friede, Verlag Chemie, D 6940 Weinheim, 1975. The spectral lines characteristic of each of the metals are also listed in this work.

In order to be able to observe the arc from a close proximity, in particular an optical device transmitting the rays by means of glass fibers is used. This optical device may be protected by non-interfering and constantly varying adapters, for example in the form of rolled foil (day light projector principle) or deflecting mirrors.

In the process according to the invention therefore for example the intensity of a characteristic spectral line of an applied metal is determined. This metal should preferably not be present in the workpiece to be welded or in the wire electrode of the burner or only in slight proportions. It has been found favorable to have the applied metal present in proportions lower than 5% and in particular 1%.

The metal may be applied to the workpiece to be welded by flame spraying or plasma spraying. The arc-spray method is for example one of these processes.

The metal may further be applied in the form of a powder. This powder may consist of a metal in the elemental form or a metal alloy. It shall be referred in the following discussion as metal powder. The process according to the invention will become more apparent below from the description of the use of such a metal powder.

As set forth above, the metal powder is applied to the edge or surface of at least one workpiece to be welded. If the burner in the course of welding deviates from the center of the weld, the intensity of the characteristic spectral line varies. If the burner deviates for example from the center of the weld toward the workpiece to which the metal powder has been applied, the quantity of the metal evaporated increases and a higher intensity of the spectral line measured is observed.

If the arc on the other hand leaves the predetermined joint line in the direction of the workpiece to which no metal powder has been applied, the amount of the metal evaporated from the metal powder applied, decreases. The intensity of the spectral line measured therefore decreases.

By means of the data determined in this manner, the arc may then be controlled with the aid of a computer and the burner guided in the center of the predetermined joint.

If the metal powder is applied to the edge on one workpiece only, the preferred mode of operation is to compare the intensity of the emitted spectral line of the metal examined with a given intensity by means of a computer and to regulate the welding burner accordingly.

In this manner, information may be obtained additionally relative to the quality of the weld. A nonuniform guidance of the weld thus is indicated by a variation of the observed or measured spectral lines. From the variation of the predetermined intensities of the spectral lines observed, information may therefore be obtained concerning the quality of the weld. Consequently, variations in intensity are indications of the homogeneous composition of the weld bath and the weld itself.

If the metal powder consists of a single metal, a metal is used that under normal conditions is stable in the elemental form. In the process, either in the elemental form or in the form of an alloy, metals are used which do not interfere with the welding process and do not have a detrimental effect on the quality of the weld. The following metals are used preferably: Fe, Mn, V, Cu, Ti, Co, Nb, Ni, Mo, W, Cr, Zr, Ta, Hf, Ir, Os, Re, Ru, Rh, Al, Be, Ce, Ge, Au, La, Pd, Pt, Sc, Ag and U. Particularly preferred are the following metals: Fe, Mn, V, Cu, Ti, Co, Nb, Ni, Mo, W, Cr, Zr, Ta, Hf and Be.

A metal powder with a grain size of 0.1 to 500 μm, in particular from 1 to 150 μm, is applied preferably, with the maximum of the grain size distribution being located between 1 and 80 μm.

The metal powder used may consist of a single metal or a metal alloy. In the latter case not merely the characteristic spectral line of one metal but of several metals, may be used for the intensity measurement.

In a preferred form of embodiment of the process according to the invention, a metal powder is applied to the edges or surfaces of all of the workpieces to be welded. Therefore, if two workpieces are to be welded together, a metal powder is applied to both surfaces or edges.

However, these metal powders have different compositions. Thus, the metal powder applied to one surface contains at least one metal that is not present in the metal powder applied to the other surface.

In this case again a metal powder may be used which consists either of a metal or a metal alloy. Mixtures of two or more metal powders may also be applied.

The welding of two workpieces may be carried out for example as follows. Two different metal powders, each consisting of a single metal, are used and one of the powders is applied to one workpiece and the other metal powder to the other workpiece. In the course of the welding the intensity of a spectral line of both metals is measured and the burner is guided in a manner such that both spectral lines are as intensive as possible.

In this fashion a guidance of the weld burner in the center of the joint is obtained. If said burner deviates from the center of the joint, the intensity of one of the spectral lines will increase, while the intensity of the other one decreases.

It is obviously also possible to compare the measured intensity of the spectral lines with a predetermined intensity and to control the arc by means of this data. It is further possible to use the data accumulated merely for quality control. The arc may also be controlled in a manner such that upon a deviation of the measured intensity from the given intensity the burner is stopped.

In this preferred form of embodiment metal alloys may again be used. Preferably, these alloys consist of metals which are not present in the metal alloy applied to the other workpiece or only in such slight proportions that the intensity of the corresponding spectral line is very low.

The type of metals, the grain size and the grain size distribution are as stated above. It should be noted in this context that metals which burn in the pure form and/or in a fine distribution, or are oxidized by contact with air, are used in the form of an alloy in order to avoid the abovementioned phenomena. This is true for example for zirconium, titanium and vanadium.

Advantageously, the metal powder is applied to the edge or surface to be welded as uniformly as possible.

It is possible for example to provide the workpieces to be welded with an adhesive coating and to apply the metal powder to it.

To insure the most uniform application possible of the metal powder, the latter is preferably mixed into a coating or adhesive medium, in particular a lacquer. This lacquer is then applied to the surface or edge to be welded.

Another object of the invention is therefore a coating medium, in particular a lacquer consisting of a binder and optionally a solvent, containing the metal powder.

As the binder, substances are chosen which evaporate without residue in the arc. These include for example polyvinylbutyral, PUR, EPO, alkyd and acryl binders. They may be physically drying resins, such as polyvinylbutyral and polyacrylate resins, and two-component masses of epoxy, polyurethane and acryl resins hardenable by means of a hardener.

The metal powder has preferably a grain size of 0.1 to 500 μm, in particular 1 to 150 μm, with the maximum of the grain size distribution being between 1 and 80 μm. A grain size of 1 to 70 μm is especially preferred.

The metal powder preferably amounts to 5 to 90% by weight and in particular to 25 to 50% by weight.

The lacquer preferably contains additives preventing the settling of metal particles and assuring a homogeneous distribution of the metal particles, thereby introducing run-off stability. These additives include in particular finely distributed aluminum and magnesium silicates, silica, soy lecithins, metallic soaps and silicone oils, higher polycarboxylic acids and polycarbonates. Thus for example, finely distributed silica marketed under the designation of Aerosil, may be used.

Any conventional solvent compatible with the binder or binder-hardener combination, may be employed. Thus for example xylene, methylglycolacetate and butylacetate may be used, together with their mixtures.

A colorant may further be added to the lacquer. Thus it is advantageous for example to color the lacquer differently according to the metal powder employed, thereby indicating the type of metal powder present in the lacquer.

A lacquer composition according to the invention consists for example of:
5–90% by weight metal powder
5–40% by weight resin (binder and hardener)
0–5% by weight additives, in particular inorganic fillers
0–1% by weight colorants
0–50% solvents.

The lacquer is applied as uniformly as possible to the surfaces and edges to be welded in order to obtain a defined thickness of the layer. The lacquer may be applied by immersion, spraying, rolling, etc.

A further object of the invention is thus the use of one of the aforedescribed lacquer compositions in a process for the guidance and/or control of the weld in electric arc welding.

The process of the invention may be employed not only to guide the weld, but also to control the welded joint. If it is found for example that the intensity of a spectral line measured is becoming too high or too low in the course of welding, the corresponding data may be stored for example in an EDV (electronic data processing) installation. The location involved may be corrected by rechecking and possibly rewelding, immediately or later.

The data obtained by the process according to the invention thus makes possible an indirect quality control of the weld.

The process of the invention may further be combined with other known sensor systems for the positioning and guidance of the weld.

To ascertain whether the metal powders contained in a lacquer are actually built into the weld, the weld of an uncoated specimen and of several specimens coated on both sides with different lacquers were examined by means of emission spectroanalysis.

The workpieces welded consisted of iron sheets according to DIN standards. The weld wire consisted of Mn, Fe and Si and was encased in a thin copper sheathing. The electrode was made of tungsten.

The weld of the uncoated specimen contained metals in the following proportions: Co=0.4%; Ti=0.05%; Nb=0.001%; Cu=0.24%; Zr=0.001%; W=0.001% and Mo=0.003%; rest Fe.

The following metal powders were employed in the case of the specimens coated with differently doped lacquers:

| Specimen 1: | titanium powder and cobalt powder |
| --- | --- |
| 2: | cobalt powder and niobium powder |
| 3: | titanium powder and niobium powder |
| 4: | tungsten powder and metal powder of an alloy consisting of copper and zirconium |
| 5: | a mixture of tungsten/vanadium powder and niobium powder. |

Analysis of the coated specimens showed that the weld contained the abovementioned metals in the following proportions:

| Specimen 1: | Ti = 0.30%; Co = 0.59%; |
| --- | --- |
| 2: | Co = 0.30%; Nb = 1.41% |
| 3: | Ti = 0.15%; Nb = 0.72% |
| 4: | W = 0.33%; Cu = 0.47% and Zr = 0.82% |
| 5: | W = 0.31%, V = 0.11% and Nb = 0.56%. |

These results show that the metals applied in the form of metal powders were incorporated in the weld.

Certain examples of the lacquer compositions that may be employed according to the invention are described below.

EXAMPLE 1

Lacquer with the following composition:

| titanium powder with a grain size of 150 μm | 28.0% by weight |
| --- | --- |
| solvent mixture of xylene, methylglycol acetate and butyl acetate | 50% by weight |
| polyvinylbutyral | 16% by weight |
| Aerosil | 5% by weight |
| Neo-Zapon orange (Zapon dye of BASF) | 1% by weight |
| Detection and control: spectral line Ti: 489.173 nm | |

EXAMPLE 2

Lacquer with the following composition:

| niobium powder (grain size 10 μm) | 50% by weight |
| --- | --- |
| polybutylacrylate | 14% by weight |
| solvent mixture of butylacetate and methylisobutyltetone | 31% by weight |
| Aerosil | 4.5% by weight |
| Zapon genuine-green | 0.5% by weight |

In these examples metal powders of cobalt, molybdenum, tungsten, chromium, nickel and of a (65%:35%) copper-zirconium alloy may also be used.

EXAMPLE 3

Lacquer with the following composition:

| molybdenum powder (grain size 10 μm) | 20% by weight |
| --- | --- |
| polymethylmethacrylate | 10% by weight |
| Thixatrol ST | 1.5% by weight |
| butylacetal | 20% by weight |
| xylene | 1.5% by weight |
| polycarbonate | 0.5% by weight |
| dye (Zapon) | 0.5% by weight |
| propylacetate | 10% by weight |
| ethylglycol | 36% by weight |
| Detection and control: spectral line Mo: 379.825 nm | |

EXAMPLE 4

Lacquer with the following composition:

| nickel powder, Inco Type 255 | 45% |
| --- | --- |
| Desmophen 55oU Bayer AG | 10% |
| Aerosil | 3% |
| silicone oil | 2% |
| butylacetal | 30% |
| methylisobutylketone | 9.5% |
| dibutyltin-dilaurate | 0.5% |

Hardening was effected with Desmodur N 3200 (Bauer AG) in a stoichiometric proportion (but hardening may also be effected by under- or over-cross-linking).

EXAMPLE 5

Lacquer having the following composition:

| tungsten powder, grain size 1 μm | 30% |
| --- | --- |
| vanadium, grain size 20 μm | 10% |
| (the vanadium powder was processed under a protective argon atmosphere) | |
| polymethylmethacrylate | 15% |
| nitrocellulose | 5% |
| Aerosil | 3% |
| ethylglycol | 15% |
| butylacetate | 22% |
| Detection and control: spectral line W: 430.21 nm V: 437.924 nm | |

In the abovedescribed examples in particular metal powders of cobalt, chromium and a copper-zirconium (65%:35%) alloy may also be used.

In this example, the lacquer also serves to protect the vanadium powder.

With reference to the drawing, there is shown an apparatus for practicing the invention as described herein. The apparatus includes a burner 1 disposed above a workpiece 2 and a workpiece 4 to which a weld 3 is applied therebetween. An optical device 5 observes the arc produced by burner 1 and transmits the rays through an optical glass fiber 6 to an apparatus 7 which provides an emission spectral analysis of the emitted spectrum. The spectral data obtained from apparatus 7 is used to control and/or guide the welding arc.

We claim:

1. A process for controlling, guiding or controlling and guiding the production of a weld seam during the electric arc welding of workpieces, which process comprises the steps of:
    (a) applying an elemental metal or an elemental metal alloy to an edge or surface of at least one workpiece, wherein the elemental metal or at least one of the metals of the elemental alloy is either not present or present in slight proportions only in the workpiece;
    (b) applying a welding arc to the workpiece provided with the elemental metal or elemental metal alloy applied thereto;
    (c) spectroanalytically observing at least one characteristic spectral line in the arc emitted by at least one metal of the applied elemental metal or elemental metal alloy and deriving spectral data therefrom; and
    (d) controlling, guiding or controlling and guiding the arc in response to the spectral data so derived.

2. The process of claim 1 wherein two workpieces are welded together, and further including the steps of:
    (a) applying a first elemental metal or an elemental metal alloy to a surface or edge of one workpiece;
    (b) applying a second elemental metal or metal alloy to a surface or edge of the other workpiece, wherein the second elemental metal alloy contains at least one elemental alloy metal not present in the first elemental metal alloy; and
    (c) spectroanalytically observing a characteristic spectral line of the elemental metal or elemental alloying metal applied to the other surface or edge.

3. The process of claim 1 wherein the elemental metal or the elemental alloy includes a metal selected from the group consisting of Fe, Mn, V, Cu, Ti, Co, Nb, Ni, Mo, W, Cr, Zr, Ta, Hf, Ir, Os, Re, Ru, Rh, Al, Be, Ce, Ge, Au, La, Pd, Pt, Sc, Ag, U and alloys thereof.

4. The process of claim 3 wherein the elemental metal or elemental metal alloy includes a metal selected from the group consisting of Mn, V, Cu, Co, Ni, Nb, Cr, Mo, Be, W and alloys thereof.

5. The process of claim 1 further including the step of applying the elemental metal or the elemental metal alloy in powder form.

6. The process of claim 5 wherein the powder is of a grain size within the range of 0.1 to 500 μm, with a maximum grain size distribution being between 1 and 80 μm.

7. The process of claim 6 wherein the powder has a grain size of from 1 to 150 μm.

8. The process of claim 1 further including applying the elemental metal or the elemental metal alloy in powder form in a coating medium.

9. The process of claim 8 wherein the coating medium includes a lacquer.

10. The process of claim 9 wherein the lacquer comprises a binder, a solvent and an elemental metal or an elemental metal alloy.

11. The process of claim 10 wherein the elemental metal or elemental metal alloy includes an element selected from the group consisting of Fe, Mn, V, Cu, Ti, Co, Nb, Ni, Mo, W, Cr, Zr, Ta, Hf, Ir, Os, Re, Ru, Rh, Al, Be, Ce, Ge, Au, La, Pd, Pt, Sc, Ag, U and alloys thereof.

12. The process of claim 11 wherein the elemental metal or elemental metal alloy includes a metal selected from the group consisting of Mn, V, Cu, Co, Ni, Nb, Cr, Mo, Be, W and alloys thereof.

13. The process of claim 10 wherein the elemental metal or elemental metal alloy is in powder form and further including an additive to prevent settling of the powder and maintaining a homogeneous distribution of the powder, the additive including an element selected from the group consisting of finely distributed aluminum silicate, finely distributed magnesium silicate, silica, waxes, soy lecithins, metallic soaps, silicone oils, polycarbonates and mixtures thereof.

14. The process of claim 10 wherein the elemental or elemental metal alloy is present in an amount of 5 to 90% by weight.

15. The process of claim 14 wherein the elemental metal or elemental metal alloy is present in an amount of from 25 to 50% by weight.

* * * * *